(12) United States Patent
Maldini et al.

(10) Patent No.: US 10,167,144 B2
(45) Date of Patent: Jan. 1, 2019

(54) DEVICE FOR REPOSITIONING TUBES IN A TUBE RACK

(71) Applicant: Roche Diagnostics Operations, Inc., Indianapolis, IN (US)

(72) Inventors: Michael Maldini, Kriens (CH); Gottlieb Schacher, Lenk im Simmental (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 221 days.

(21) Appl. No.: 14/945,473

(22) Filed: Nov. 19, 2015

(65) Prior Publication Data

US 2016/0159579 A1    Jun. 9, 2016

(30) Foreign Application Priority Data

Dec. 2, 2014   (EP) ..................................... 14195832

(51) Int. Cl.
    *B65G 47/24*    (2006.01)
    *B25J 13/08*    (2006.01)
    (Continued)

(52) U.S. Cl.
    CPC ............ *B65G 47/24* (2013.01); *B25J 13/083* (2013.01); *B65B 21/12* (2013.01); *B65B 21/18* (2013.01);
    (Continued)

(58) Field of Classification Search
    CPC ......... B65G 47/24; B65B 21/12; B65B 21/18; B65B 57/14; G01N 35/0099;
    (Continued)

(56) References Cited

U.S. PATENT DOCUMENTS 3,553,932 A * 1/1971 Rowekamp ............. B65B 21/18
                                                                53/247
3,971,190 A * 7/1976 McGill ................... B65B 21/18
                                                                414/618

(Continued)

FOREIGN PATENT DOCUMENTS

GB            917417 A    2/1963
GB            931490 A    7/1963
            (Continued)

*Primary Examiner* — Lynn E Schwenning
(74) *Attorney, Agent, or Firm* — Roche Diagnostics Operations, Inc.

(57) ABSTRACT

A device for repositioning tubes in a tube rack is presented. The device comprises a base; a mount movable relative to the base in a first and second direction; an actuator for moving the mount; grippers coupled to and movable with the mount, each gripper comprising arms with portions for gripping a tube; a biasing element coupled to the mount and to the arms to be movable relative to the mount and to move the portions towards/away from each other; a blocking element coupled to the base to engage the biasing element and to block movement of the biasing element with respect to the mount against a force where the mount is moved in the first direction to move the portions towards each other and to disengage from the biasing element when the mount is moved in the second direction to allow the portions to be moved apart.

13 Claims, 5 Drawing Sheets

(51) Int. Cl.
*B65B 21/12* (2006.01)
*B65B 21/18* (2006.01)
*B65B 57/14* (2006.01)
*G01N 35/00* (2006.01)
*G01N 35/04* (2006.01)

(52) U.S. Cl.
CPC ......... *B65B 57/14* (2013.01); *G01N 35/0099* (2013.01); *G01N 2035/0406* (2013.01); *G01N 2035/0412* (2013.01); *G01N 2035/0494* (2013.01)

(58) Field of Classification Search
CPC ... G01N 2035/0406; G01N 2035/0412; G01N 2035/0494
USPC .......................................................... 414/783

See application file for complete search history.

(56) References Cited

U.S. PATENT DOCUMENTS

| | | | | |
|---|---|---|---|---|
| 4,787,662 | A | * | 11/1988 | Dewez ................... B65G 47/91 294/65 |
| 6,177,050 | B1 | | 1/2001 | Bybee et al. |
| 6,440,368 | B1 | * | 8/2002 | Cohen .................... G01N 35/04 422/561 |
| 2008/0181757 | A1 | * | 7/2008 | Wheeler ................. B25J 9/104 414/738 |
| 2012/0253516 | A1 | | 10/2012 | Iida |
| 2013/0274913 | A1 | * | 10/2013 | Wilson ................ B65G 1/0478 700/214 |
| 2015/0298321 | A1 | * | 10/2015 | Gross ................... B65G 11/023 422/67 |
| 2016/0154017 | A1 | * | 6/2016 | Oguri et al. ......... G01N 35/025 198/678.1 |

FOREIGN PATENT DOCUMENTS

| | | |
|---|---|---|
| WO | 1990/003834 A1 | 4/1990 |
| WO | 2012/018993 A1 | 2/2012 |

* cited by examiner

DEVICE FOR REPOSITIONING TUBES IN A TUBE RACK

CROSS-REFERENCE TO RELATED APPLICATIONS

This application claims priority to EP 14195832.3, filed Dec. 2, 2014, which is hereby incorporated by reference.

BACKGROUND

The present disclosure generally relates to the field of analytical sample processing and, in particular, relates to a device for repositioning tubes in a tube rack.

In automated clinical analyzers liquid samples such as bodily fluids can be tested by various diagnostic methods. In practical use, it is convenient to supply samples for analysis in tubes with the tubes being placed on tube racks.

Sample processing by analyzers usually involves pipetting aliquots of samples. Due to the fact that pipetting operations typically require that the pipettes are lowered into the tubes, it is important that the tubes have an upright position in the tube rack to avoid any physical contact between pipettes and tubes which are likely to result in a contamination of samples and even damage of pipettes or tubes. However, tubes usually have at least a small position variability in their holding seats so that the tubes can readily be inserted in or removed from the tube rack, e.g., by manual interaction. Accordingly, a situation can occur that tubes are not properly fit in the holding seats, that is to say, have a too high position in the tube rack by not reaching the bottom face of a holding seat and, thus, may have a slightly tilted orientation relative to an upright position. This can, e.g., be caused by moving the tube rack in the course of sample processing or improper handling of a technician. It is also possible that if a tube is not properly positioned in a holding seat, the tube may crash with instrument parts during conveyance of a tube rack.

Therefore, there is a need for an automated device for repositioning tubes in a tube rack to ensure that tubes are properly positioned in the tube racks.

SUMMARY

According to the present disclosure, a system, process and a device for repositioning tubes in a tube rack is presented. The device can comprise a stationary base, a mount movable relative to the base in a first moving direction and a second moving direction opposite to the first direction, at least one actuator for moving the mount, and one or more grippers coupled to the mount and movable with the mount. Each gripper can comprise a pair of gripping arms provided with gripping portions for gripping a tube. The device can further comprise at least one biasing element resiliently coupled to the mount and to the gripping arms in a manner to be movable relative to the mount and thereby move the gripping portions towards or away from each other and at least one blocking element resiliently coupled to the stationary base configured to engage with the biasing element and to block movement of the biasing element with respect to the mount against a resilient force during a first period in which the mount is moved in the first moving direction so as to move the gripping portions towards each other and configured to disengage from the biasing element before a second period in which the mount is moved in the second moving direction so as to allow the gripping portions to be resiliently moved away from each other.

Accordingly, it is a feature of the embodiments of the present disclosure to provide for a system, a process and an automated device for repositioning tubes in a tube rack to ensure that tubes are properly positioned in the tube racks. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
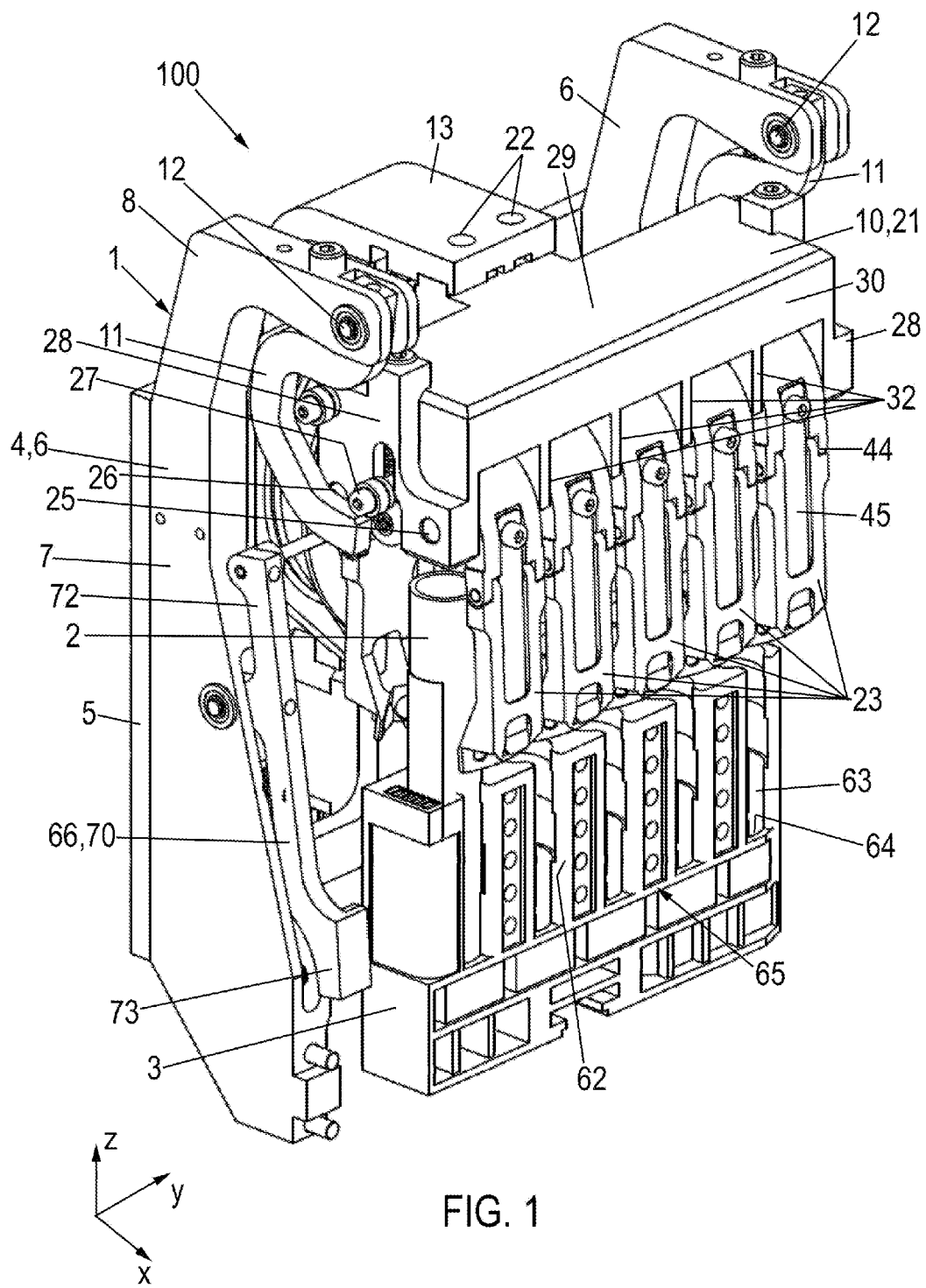
FIG. 1 illustrates a combined side and front view of the device together with an exemplary tube rack according to an embodiment of the present disclosure.
Figure 2:
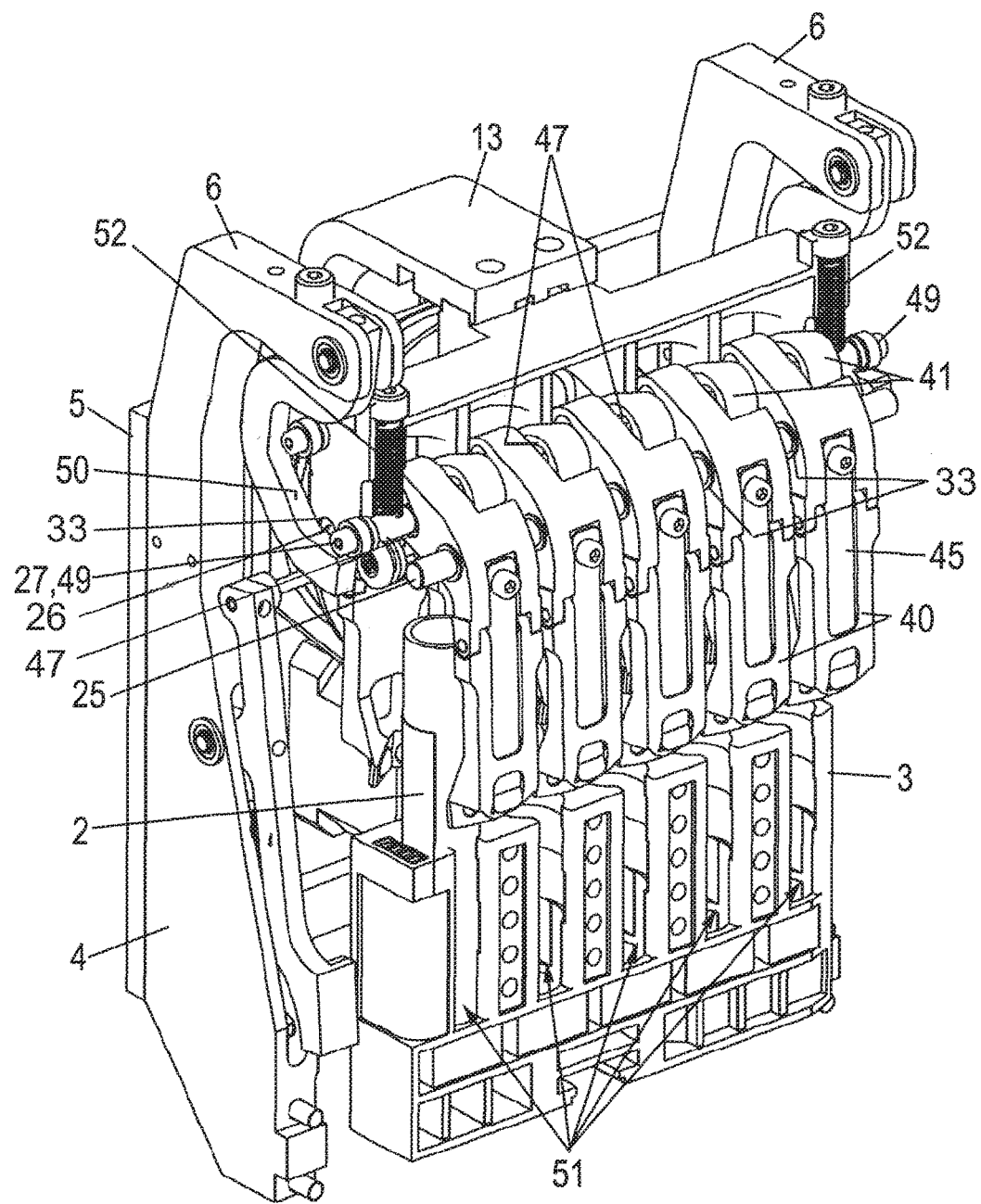
FIG. 2 illustrates another combined side and front view of the device of FIG. 1 according to an embodiment of the present disclosure.
Figure 3:
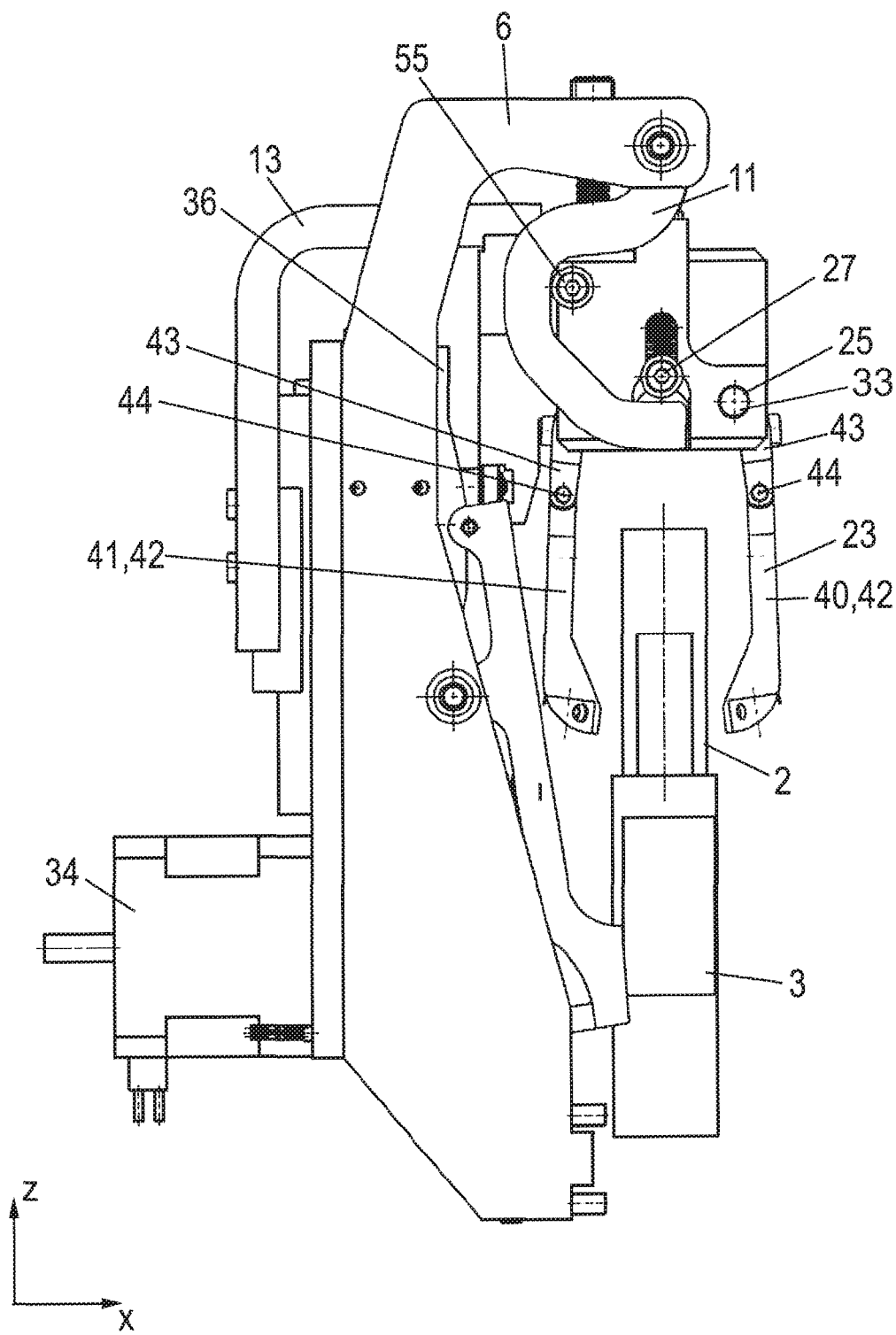
FIG. 3 illustrates a side view of the device of FIG. 1 according to an embodiment of the present disclosure.
Figure 4:
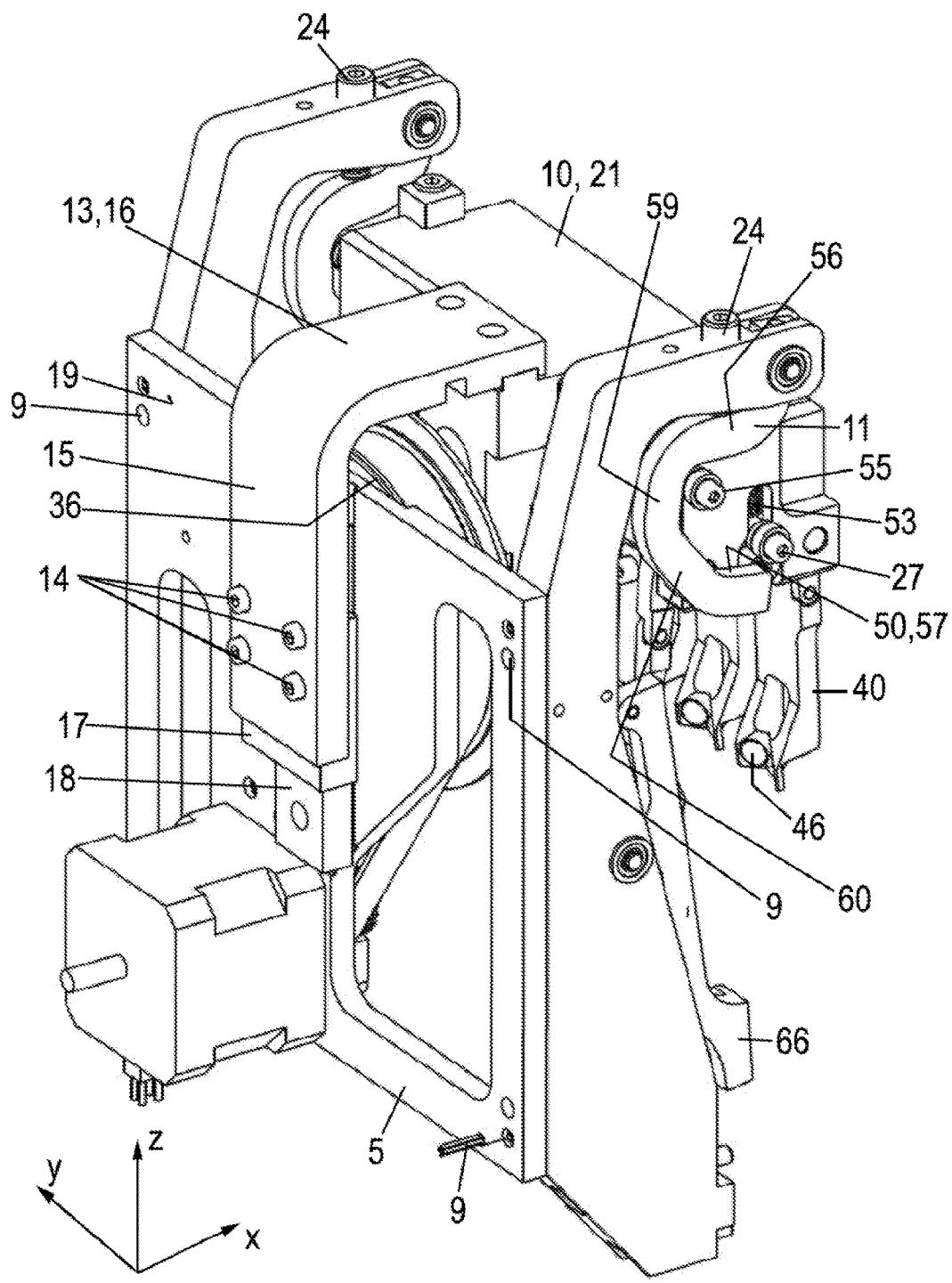
FIG. 4 illustrates a combined side and rear view of the device of FIG. 1 according to an embodiment of the present disclosure.
Figure 5:
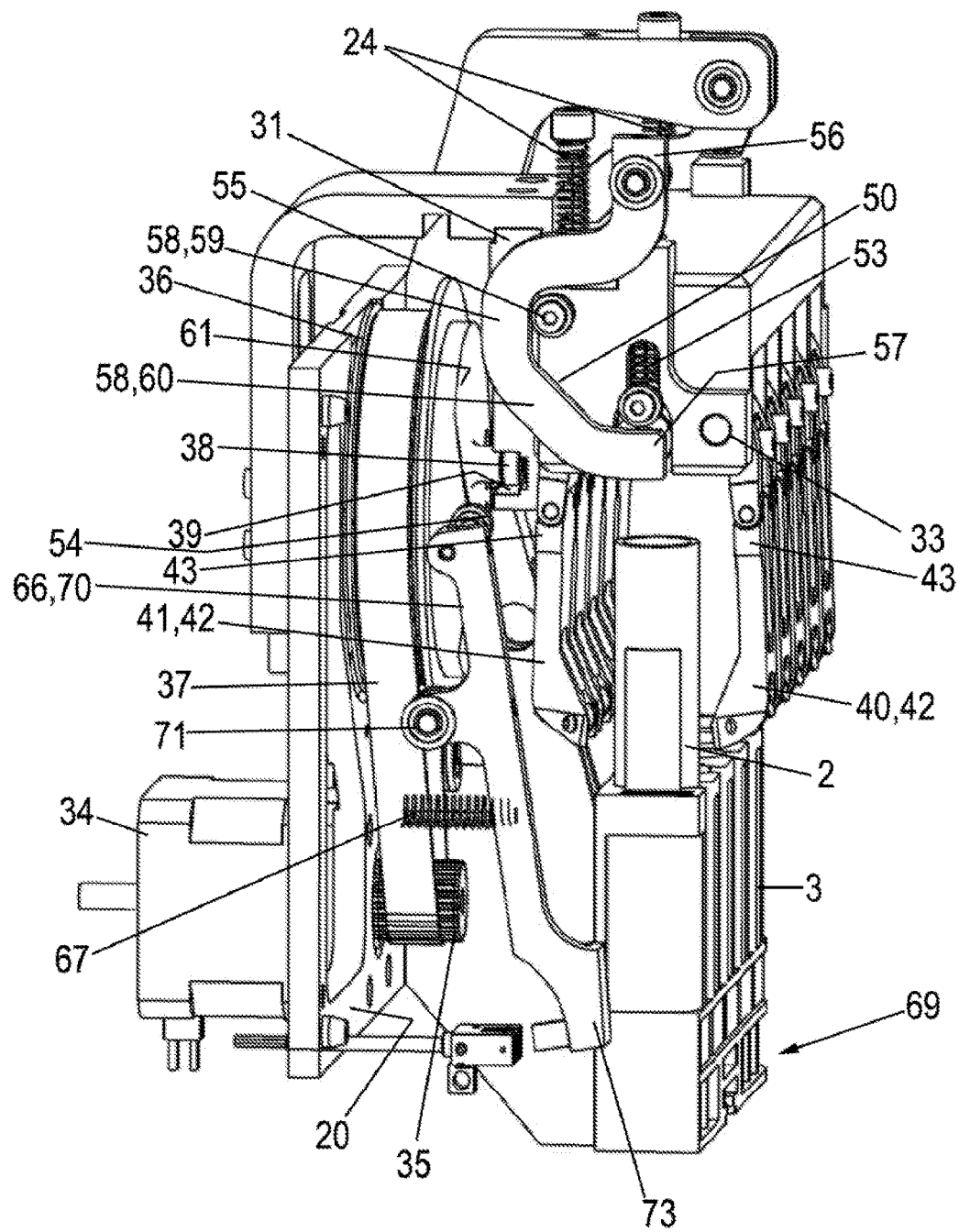
FIG. 5 illustrates another side view of the device of FIG. 1 according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

As used herein, the term "tube" can relate to an elongate vessel adapted for receiving a sample. In one embodiment, the tube can have a generally cylindrical shape with a closed, for example, rounded, bottom at one end and a top opening at the other end.

As used herein, the term "tube rack", interchangeably referred to as "rack", can relate to any device configured to provide one or more regions, each of which being capable of holding one tube, in the following denoted as "holding seats". Typically, each holding seat can comprise a hollow space formed by a seat wall and a seat bottom, configured to insert a tube in an upright position. The bottom seat can be the lowest part of a holding seat. In one embodiment, the tube rack can have only one holding seat and can be configured as single-tube holder or puck. In one embodiment, the tube rack can have a plurality of holding seats arranged in a one-dimensional or two-dimensional array and can be configured as multi-tube holder.

Generally, each holding seat of the tube rack can be configured to hold a tube in upright position. As used herein, the term "upright" can relate to a parallel (non-tilted) orientation of a longitudinal axis (direction of extension) of the tube relative to a direction perpendicular to a rack plane as defined by the one- or two-dimensional array of holding seats. Specifically, the upright position of a tube can be identical to a vertical orientation (direction of gravity), with the rack plane having a horizontal orientation. Accordingly, the term "tilted" can relate to a non-parallel orientation of the longitudinal axis of a tube with respect to the upright position.

As used herein, the term "reposition" can relate to changing the position of a tube from a non-contact position with respect to the seat bottom to a position of contact with the seat bottom. Repositioning thus can comprise pushing a tube towards the seat bottom until contact with the seat bottom is established. As a result, repositioning may comprise changing the orientation of a tube contained in a tube rack from a tilted orientation to a non-tilted (upright) orientation. Accordingly, the reposition of a tube may not involve putting a tube for the first time into a holding seat. Instead, repositioning of a tube can relate to changing the vertical position and/or the orientation of a tube yet contained in a holding seat typically involving fully inserting the tube into the holding seat, that is to say, moving the tube towards a bottom of the holding seat until the tube lies against the bottom face thereby having physical contact with the bottom face.

A device for repositioning one or more tubes in holding seats of a tube rack is proposed. The device can be configured in various ways in accordance with the specific demands of the user and, e.g., can be used in connection with automated analyzers for analyzing samples by various analytical methods such as, but not limited to, clinical-chemical, immunochemical, coagulation, haematology, urinalysis and biochemical analysis, in general. Specifically, the device for repositioning tubes in a tube rack can comprise a stationary base non-movable with respect to the surroundings at least during operation of the device.

The device further can comprise a mount, movable relative to the stationary base in a first moving direction for moving the mount towards the tube rack, i.e. one or more holding seats, and a second moving direction, opposite to the first moving direction, for moving the mount away from the tube rack, i.e., one or more holding seats. Specifically, in one embodiment, the device can be configured in such a manner that the first and second moving directions correspond to the direction of extension of the one or more tubes having an upright position in the tube rack. In one embodiment, the mount can be linearly movable relative to the base.

The device can further comprise at least one actuator for moving the carrier. In one embodiment, the actuator can be an electric motor having an actively rotated rotor. In one embodiment, the rotor can be rotatably coupled to an eccentric, with the eccentric being engaged with a guidance of the mount such as, but not limited to, linear guidance, in particular, a notch for moving the mount in the first and second moving directions. This can provide an easy, robust and cost-efficient method of moving the mount.

The device can further comprise one or more grippers coupled to the mount and movable with the mount. Each of the grippers can comprise a pair of gripping arms with gripping portions for gripping a tube. Each of the one or more grippers can be configured to grip a tube from the side below a top opening of the tube. In one embodiment, each of the one or more grippers can be configured to grip a tube at least 20% of a length of a tube below a top opening of the tube. Accordingly, contact of the gripper with either an open top opening or with a cap closing the top opening can be prevented and therefore possible cross-contamination of samples contained in the tubes can be avoided. In one embodiment, the gripping portion of each of the gripping arms can comprise a rubber pad for gripping a tube. Accordingly, tubes can reliably be gripped by the gripper arms with the friction force readily adaptable by the rubber pads. Typically, a rubber pad can readily be replaced, e.g., while performing a maintenance operation.

The device can further comprise at least one biasing element resiliently coupled to the mount and coupled to the gripping arms in a manner to be movable relative to the mount and thereby move the gripping portions towards or away from each other.

The device can further comprise at least one blocking element resiliently coupled to the stationary base and configured to engage with the biasing element and to block movement of the biasing element with respect to the mount against a resilient force during a first period in which the mount is moved in the first moving direction so as to move the gripping portions towards each other and configured to disengage from the biasing element before a second period in which the mount is moved in the second moving direction so as to allow the gripping portions to be resiliently moved away from each other.

The device can thus advantageously make it possible to reposition tubes in a tube rack in order to avoid any collision between tubes and pipettes during following pipetting operations usually performed in the process of sample analysis or between tubes and parts of the instrument during rack conveyance. Hence, a major advantage can be given by the fact that collisions can be avoided and therefore damage of tubes and/or pipettes as well as spillage of samples and process interruptions can be avoided. Accordingly, samples can reliably be processed in a time- and cost-efficient manner.

In one embodiment, the device can be configured such that each gripper gripping a tube can slide (slip) along the tube when the mount is moved in the first moving direction and the tube is fully inserted in a holding seat. Accordingly, application of unnecessary force against the seat bottom that may result in tube damage and/or gripper damage can be prevented. Also, tilted and non-tilted tubes in a tube rack can advantageously be handled in the same manner in order to reposition the tilted tubes in an upright position.

In one embodiment of the device, the gripping arms can be resiliently deformable. As a result, a sliding grip of a gripper when the mount is moved in the first moving direction and the gripped tube is fully inserted in a holding seat can easily be realized. Another advantage can be given by the fact that the gripping arms can readily adapt to tubes having different dimensions perpendicular to their extensions so that both larger and narrower tubes in a same tube rack can reliably be repositioned. Specifically, in one embodiment, each of the gripping arms can comprise a gripping portion for gripping a tube and a fixing portion for rotatably fixing (pivotably coupling) the gripping arm to the mount and can further comprise a leaf spring arranged in such a manner that the gripping portion can resiliently be bent relative to a fixing portion coupled to the biasable element. As a result, the gripping arm can be manufactured in a robust and cost-efficient manner with the resilient force readily adaptable to the specific needs of the user. Furthermore, leaf springs can easily be replaced if required. In one embodiment, the gripping portion can be articulated to the fixing portion so that the gripping portion can easily be bent relative to the gripping portion. As a result, adaptation of the gripping arms to tubes having different widths can be further improved.

In one embodiment of the device, the mount can comprise a first holding rod and a second holding rod and each gripper can comprise a first gripping arm pivotably coupled to the first holding rod and a second gripping arm pivotably coupled to the second holding rod. As a result, the gripping arms can be rotatably coupled to the mount in an easy, robust and cost-efficient manner.

In one embodiment of the device, the biasing element can be a biasing rod which can be resiliently coupled to the mount by a resilient element such as, but not limited to, a spring, e.g. a helical spring, and can be coupled to both the first and second gripping arms with each gripping arm coupled to the biasing rod in such a manner that a movement of the biasing rod can cause pivoting of the gripping arms around the first holding rod and the second holding rod, respectively. Accordingly, the gripping arms can be rotated around the first and second holding rod respectively so that the gripping portions can be moved towards each other against the resilient force of the resilient biasing rod and can also be moved away from each other by the resilient force of the resilient biasing rod. As a result, the gripping portions can be moved towards and away from each other in an easy, robust and cost-efficient manner. In one embodiment, the device can be configured such that the biasing rod can be moved parallel to the first and second moving directions, respectively, of the mount. In one embodiment, the device can be configured such that the biasing rod can be kept stationary with respect to the base at least during a part of the first period for moving the mount in the first moving direction and can be moved relative to the base and relative to the mount at least during the second period for moving the mount in the second moving direction. In one embodiment, each gripping arm can be coupled to the biasing rod in such a manner that movement of the biasing rod can cause pivoting of the gripping arms around the first holding rod and the second holding rod, respectively, wherein pivoting of the gripping arms can be stopped prior to moving the mount in the second moving direction. In one embodiment, the first and second gripping arms can be coupled to the biasing rod via elongated holes, with the biasing rod inserted through the elongated holes, such that the biasing rod can be moved relative to the gripping arms, e.g. in the first and second moving directions of the mount. As a result, the device can be easily manufactured in robust and cost-efficient manner. Furthermore, maintenance of the device can be facilitated.

In one embodiment of the device, the blocking element can be a lever, pivotably fixed to the base. The lever can be configured in such a manner that the biasing element can be or can get in contact with the lever during the first period and subsequently slides off the pivoted lever before the second period. As a result, blocking and release of the biasing element while moving the mount in the first and second moving directions can easily be realized.

In one embodiment, the device can further comprise a stopper configured to stop a tube rack transported on a rack transport line. Specifically, in one embodiment, the stopper can be a pivoted arm resiliently coupled to the base in such a manner that the arm can be pivoted against a resilient force. As a result, a tube rack can be kept stationary relative to the one or more grippers so that the grippers can grip tubes for repositioning when moving the mount in the first moving direction.

A system for repositioning tubes in a tube rack is also presented. The system can comprise a tube rack holding one or more tubes and a device for repositioning tubes in the tube rack as above-described. In one embodiment, the system can comprise a rack transport line configured to transport the tube rack into a position allowing repositioning of tubes by the device for repositioning tubes in the tube rack.

A process for repositioning a tube in a holding seat of a tube rack using a gripper is also presented. The process can comprises moving the gripper in a first moving direction during a first period towards the tube rack; moving the gripper in a second moving direction, opposite to the first moving direction, during a second period, after the first period; gripping the tube by the gripper within the first period; and releasing the tube before the second period. In one embodiment, the gripper can slidably grip a tube if the tube is fully inserted in a holding seat of the tube rack.

By way of illustration, specific exemplary embodiments are now described. In the following description, reference is made to first to third directions (x, y, z), perpendicularly aligned with respect to each other, with the first and second directions (x, y) spanning a plane and the third direction (z) being perpendicularly aligned with respect to the plane. In one embodiment, the first and second directions (x, y) can span a horizontal plane and the third direction (z) can be vertically aligned (direction of fall).

An automated system for repositioning tubes in a tube rack, generally referred to under reference numeral 100, is presented. Specifically, the system 100 can include an automated device 1 for repositioning tubes 2 in holding seats 51 of a tube rack 3. The system 100 can be operatively coupled to an analyzer for analyzing samples or to an analytical or post-analytical system (not shown), e.g. to a transport line for transporting racks to or from an analyzer.

Stated more particularly, the device 1 for repositioning tubes 2 in a tube rack 3 can include a stationary base 4 which at least during operation of the device 1 is not moved with respect to the surroundings of the device 1, e.g., a surface underneath the device 1. In one embodiment, the base 4 can comprise a rear plate 5, e.g., having a generally rectangular shape and two side plates 6, each of which can be fixed on edge to the rear plate 5, with the rear plate 5 oriented in a plane spanned by the second direction (y) and third direction (z) and each of the side plates 6 oriented in a plane spanned by the first direction (x) and third direction (z). In one embodiment, each of the side plates 6 can have an angled shape and can include a first side plate portion 7 extending in the third direction (z) and can be directly fixed to the rear plate 5 by side plate fixers 9 such as, but not limited to, screws and a second side plate portion 8 projecting away from the first side plate portion 7 in the first direction (x).

In one embodiment, at each side plate 6, the device 1 can comprise a hook 11 having a general C-shape and rotatably fixed to the second side plate portion 8 by a hook pivot joint 12 at an end portion thereof. Accordingly, each hook 11 can be rotated relative to the side plate 6 in two rotating directions, opposite with respect to each other, in a plane spanned by the first direction (x) and third direction (z). In one embodiment, at each side plate 6, a hook resilient element 24 such as, but not limited to, a helical spring can be arranged between the second side plate portion 8 and the hook 11 so as to resiliently couple the side plate 6 and the hook 11 thereby biasing the hook 11 in one rotating direction.

The device 1 can further comprise a mount 10, which, in one embodiment, can be movably coupled to the base 4 so as to be movable in a first moving direction towards the tube rack 3, i.e. towards the holding seats 51, and a second moving direction, opposite to the first moving direction, away from the holding seats 51. In one embodiment, the first and second moving directions can be parallel to the third direction (z) and can e.g. be vertically aligned. As illustrated, in one embodiment, the mount 10 can comprise a plate-like elbow 13 having an angled shape and can be slidably fixed to the base 4. Stated more particularly, the elbow 13 can comprise a first elbow portion 15 extending in the third direction (z) and a second elbow portion 16 projecting away from the first elbow portion 15 in the first direction (x). The first elbow portion 15 can be directly fixed to a carriage 17 by elbow fixer 14 such as, but not limited to, screws, with the carriage 17 slidably coupled to a linear carriage guide 18 formed at a back side 19 of the rear plate 5 and extending in the third direction (z). Accordingly, the mount 10 can be linearly translated back and forth along the carriage guide 18, e.g., towards the holding seats 51 and away from the holding seats 51 of the tube rack 3.

As illustrated, in one embodiment, the mount 10 can further comprise a carrier, generally referred to under reference numeral 21, with the carrier 21 fixed to the second elbow portion 16 at an end portion thereof by carrier fixers 22 such as, but not limited to, screws. Stated more particularly, in one embodiment, the carrier 21 can comprise a first holding rod 25 and a second holding rod 26, with each holding rod 25, 26 extending in the second direction (y) and fixed to two carrier side portions 28 of the carrier 21. As illustrated, the holding rods 25, 26 can, e.g., be inserted through fixation holes 33 of the carrier side portions 28. Each of the carrier side portions 28 can extend in a plane spanned by the first direction (x) and third direction (z). As illustrated, in one embodiment, the carrier 21 can further comprise a carrier top portion 29 extending in a plane spanned by the first direction (x) and second direction (y), a carrier front portion 30, a carrier rear portion 31, each of which can extend in a plane spanned by the second direction (y) and third direction (z), and a plurality of regularly spaced apart carrier intermediate portions 32, each of which can extend in a plane spanned by the first direction (x) and third direction (z). The various portions 28-32 of the carrier 21 can be fixed with respect to each other and together can form a stiff bottom-open casing for accommodating upper end portions of the grippers 23 in separate compartments as defined by the spaces between adjacent carrier intermediate portions 32.

As illustrated, in one embodiment, the device 1 can further comprise an actuator 34 for moving the mount 10 which, in one embodiment, can be configured as electric motor having an actively rotated rotor 35 which, in one embodiment, can be rotatably coupled to a disk 36 extending in a plane spanned by the second direction (y) and third direction (z) by a belt drive 37. The disk 36 can be rotatably fixed to the rear plate 5 at a front side 20 thereof. As a result, by actively rotating the rotor 35, the disk 36 can be rotated by the belt drive 37. In one embodiment, the disk 36 can have an eccentric disk projection 38 extending in the first direction (x) towards the carrier rear portion 31 and engaged with a linear guide such as, but not limited to, a notch 39 formed by the carrier rear portion 31. The notch 39 can linearly extend in the second direction (y). Accordingly, by rotating the disk 36, the disk projection 38 can entrain the mount 10 thereby moving the mount 10 linearly back and forth along the first and second moving directions, while the disk projection 38 is moved back and forth within notch 39 in the second direction (y). Accordingly, the rotating motion of the rotor 35 can readily be transformed to a linear motion of the mount 10.

As illustrated, each gripper 23 can comprise a pair of gripping arms 40, 41 opposed with respect to each other in the first direction (x). Accordingly, each gripper 23 can comprise a first gripping arm 40 and a second gripping arm 41, with each gripping arm 40, 41 comprising a gripping portion 42 for gripping a tube 2 and a fixing portion 43 for rotatably coupling the gripping arm 40, 41 to the mount 10. Specifically, as illustrated, in one embodiment, the fixing portion 43 can be articulated to the gripping portion 42 by a hinge 44 extending in the second direction (y). As a result, the gripping portion 42 can readily be pivoted towards and away from a tube 2 relative to the fixing portion 43. In one embodiment, each of the gripping arms 40, 41 can comprise a leaf spring 45 extending from the fixing portion 43 to the gripping portion 42 so that the gripping portion 42 can resiliently be bent relative to the fixing portion 43. As a result, each of the gripping arms 40, 41 can be resiliently deformable. Furthermore, in one embodiment, each gripping portion 42 can comprise a rubber pad 46 for gripping a tube 2.

As illustrated, in one embodiment, each fixing portion 43 can have a curved shape and can comprise a first rod hole 47, a fixation hole 33, and the hinge 44. In one embodiment, the first rod hole 47 can be formed at an end portion of the fixing portion 43 opposite to the hinge 44. In one embodiment, the fixation hole 33 can be a round hole. In one embodiment, the first rod hole 47 can be an elongated hole, e.g., having an extension following the extension of the fixing portion 43. As illustrated, the first holding rod 25 can be inserted through the fixation holes 33 of the first gripping arms 40 and the second holding rod 26 can be inserted through a fixation hole 33 of the second gripping arms 41. As a result, the first gripping arms 40 can be rotatably coupled to the first holding rod 25 and the second gripping arms 41 can be rotatably coupled to the second holding rod 26. Accordingly, the first and second gripping arms 40, 41 can be moved together with the mount 10, i.e. together with the first and second holding rod 25, 26, in the first and second moving directions, respectively and can also be rotated around the first and second holding rod 25, 26, respectively.

As illustrated, in one embodiment, the fixing portions 43 of both the first and second gripping arms 40, 41 can be arranged side by side in a row extending in the second direction (y), with the first rod holes 47 being lined up with each other. In one embodiment, the device 1 can further comprise a biasing rod 27, extending in the second direction (y) and resiliently coupled to the mount 10 by rod resilienter 52 such as, but not limited to, to a helical spring extending in the third direction (z). As illustrated, e.g., two rod resilienters 52 spaced apart with respect to each other can be envisaged. The rod resilienter 52 can, e.g., be arranged between the biasing rod 27 and a lower face of the carrier top portion 29. As illustrated, the biasing rod 27 can be inserted through the first rod holes 47 of the first and second gripping arms 40, 41 and can extend beyond the carrier side portions 28 thereby passing through rod guides 53 formed by the carrier side portions 28. Specifically, in one embodiment, two biasing rod end portions 49 can project from the carrier side portions 28 in the second direction (y). As illustrated, each of the rod guides 53 can be configured to guide the biasing rod 27 in the third direction (z), i.e. along the first and second moving directions of the mount 10, respectively.

As illustrated, in one embodiment, each of the C-shaped hooks 11, biased by the resilient force of the hook resilienter 24, can be rotated in a first rotating direction towards the biasing rod 27 so that the hook 11 can block a path of the biasing rod 27, through which path the biasing rod 27 is travelling when moving the mount 10 in the first and second moving directions. Here, rotation in the first rotating direction of each of the hooks 11 can be stopped by a carrier projection 55 projecting from each of the carrier side portions 28. As illustrated, in one embodiment, each hook 11 can comprise a first hook end portion 56 having a rightangled shape for rotatably fixing the hook 11 to the second side plate portion 8 by hook pivot joint 12, a second hook end portion 57 having a linear shape for stopping movement of the biasing rod 27, and an hook intermediate portion 58 connecting the first hook end portion 56 and the second hook end portion 57. Stated more particularly, in one embodiment, the hook intermediate portion 58 can comprise a first part 59 having a linear shape and directly connected to the first hook end portion 56, an angle of about 90° can be formed between the first part 59 and the first hook end portion 56, and a second part 60 having a linear shape and directly connected to both the first part 59 and the second hook end portion 57, an angle of less than 90° can be formed between the first part 59 and the second part 60. At least a portion of the face of the hooks 11 at the side of the carrier projection 55 can be configured as a sliding face 50. Specifically, in one embodiment, the hook intermediate portion 58 can have a sliding face 50 configured as sliding face 50 for the carrier projection 55 and the second hook end portion 57 can have a sliding face 50 configured as sliding face 50 for the biasing rod end portions 49. Here, the sliding face 50 of the hook intermediate portion 58 can be configured such that sliding of the carrier projection 55 along the sliding face 50 can cause the hook 11 to be rotated in a second rotating direction, opposite the first rotating direction, until the hook 11 is out of the path of the biasing rod 27.

As detailed above, by operating the actuator 34, the mount 10 can be moved back and forth in the first and second moving directions (e.g. third direction (z)) between an upper stop position and a lower stop position in which the moving direction changes. Specifically, moving the mount 10 in the first and second moving directions can entrain the grippers 23 by the first and second holding rods 25, 26, respectively. If the mount 10 is in the upper stop position prior to starting movement in the first moving direction during a first period, each of the carrier projections 55 is in a position that can allow the hooks 11 to be rotated in the first rotating direction so that the second hook end portions 57 can be positioned within the path of the biasing rod 27. In that rotating position, the first part 59 of the hook intermediate portion 58 can be parallel to the third direction (z), the second hook end portion 57 can be parallel to the first direction (x), and the second part 60 of the hook intermediate portion 58 can be inclined towards the biasing rod end portion 49 with respect to the first direction (x) and third direction (z).

Accordingly, when moving the mount 10 in the first moving direction during the first period starting from the upper stop position, movement of the biasing rod 27 relative to the base 4 can be blocked by the second hook end portions 57, with the biasing rod end portions 49 lying against the second hook end portions 57. As a result, the biasing rod 27 can be blocked relative to the base 4 (i.e. can be moved relative to the mount 10) thereby increasing the resilient force of the rod resilienter 52. This can cause the pair of first and second gripping arms 40, 41 of each gripper 23 to rotate around the first holding rod 25 and second holding rod 26, respectively, towards each other in order to grip a tube 2. Here, in the first period when moving the mount 10 in the first moving direction, each of the carrier projections 55 can travel along the first part 59 of the hook intermediate portion 58 so as to not cause rotation of the hooks 11 (and continue blocking of the biasing rod 28) due to that the first part 59 is in parallel alignment with the first moving direction. Then, after a travel path of the mount 10 corresponding to the linear extension of the first part 59, each of the carrier projections 55 can slide along the sliding face 50 of the inclined second part 60 of the hook intermediate portion 58 to thereby cause rotation of the hook 11 in the second rotating direction so as to move the second hook end portion 57 away from the biasing rod end portion 49. As a result, the biasing rod end portions 49 laying against the sliding faces 50 of the second hook end portions 57 can slide off the second hook end portions 57 so as to release the biasing rod 27. Then, urged by the resilient force of the rod resilienter 52, the biasing rod 27 can be pushed in the second moving direction relative to the base 4 and relative to the mount 10 thereby decreasing the resilient force of the rod resilienter 52. Here, movement of the biasing rod 27 can cause the pair of first and second gripping arms 40, 41 of each gripper 23 to rotate around the first holding rod 25 and second holding rod 26, respectively, away from each other in order to release a gripped tube 2. Specifically, in one embodiment, the device 1 can be configured such that the grippers 23 open prior to moving the mount 10 in the second moving direction during a second period following the first period starting from the lower stop position.

When moving the mount 10 in the second moving direction during the second period starting from the lower stop position, movement of the biasing rod 27 relative to the base 4 cannot be blocked by the hooks 11. As a result, the biasing rod 27 can be moved together with the mount 10. Here, in the second period when moving the mount 10 in the second moving direction, each of the carrier projections 55 can first slide along the second part 60 and then along the first part 59 of the hook intermediate portion 58 so as to allow rotation of the hooks 11 in the first rotating direction caused by the resilient force of the hook resilienter 24. The hooks 11 can then take a rotating position in which the second hook end portion 57 is in the path of the biasing rod 27. Accordingly, the biasing rod 27 can again be blocked in the next movement of the mount 10 in the first moving direction starting from the upper stop position.

Accordingly, as above-detailed, by moving the mount 10 in the first moving direction during the first period, the grippers 23 can be moved in the first moving direction, with the pair of gripping arms 40, 41 of each gripper 23 moved towards each other for gripping a tube. By moving the mount 10 in the second moving direction during the second period, the grippers 23 can be moved in the second moving direction with the pair of gripping arms 40, 41 of each gripper 23 moved away from each other for releasing a gripped tube 2.

As illustrated, in one embodiment, the tube rack 3 can be configured as multi-tube holder having a linear array of plural (e.g. five) holding seats 51 for holding tubes 2 in an upright position. In one embodiment, the number of grippers 23 can equal the number of holding seats 51. It, however, is to be understood that the number of grippers 23 can also be different from the number of tubes 2 and holding seats 51, respectively. In one embodiment, each tube 2 can be an elongate vessel for receiving a sample having a cylindrical shape with a closed (e.g. rounded) bottom at one end and an opening at the other end. Each holding seat 51 can comprise a seat wall 62 and a seat bottom 64 which together surround a hollow space 63 for receiving a tube 2. As illustrated, in one embodiment, the hollow space 63 can have a general cylindrical shape. As illustrated, in one embodiment, the holding seat 51 can be configured to receive only a lower part of the tube 2. As detailed above, the upright position of a tube 2 can relate to a parallel (non-tilted) orientation of a longitudinal axis (direction of extension) of the tube 2 relative to a direction perpendicular to a rack plane 65 as defined by the linear array of holding seats 51. In one embodiment, as illustrated, the upright position of the tubes 2 can be in parallel alignment with the third direction (z) which, e.g., can be a vertical orientation. Here, the rack plane 65 can extend in the first direction (x) and second direction (y) which, e.g., can be a horizontal orientation. Each holding seat 51 can be configured to hold a tube 2 in an upright position.

However, a situation can occur that one or more tubes 2 are not fully inserted in their holding seats 51 and in such case can have a tilted orientation relative to the upright orientation.

Having positioned the tube rack 3 in a proper position relative to the device 1, i.e. in a position in which the upright position of the tubes 2 is aligned with the path of the grippers 23 in the third direction (z), when operating the device 1, the grippers 23 can be moved towards and away from the holding seats 51. Here, when moving the mount 10 in the first moving direction (along the third direction (z)), the grippers 23 can grip the tubes 2 and, in case one or more tubes 2 are present, that are not fully inserted in the holding seats 51, can move the tubes 2 in the first moving direction until they are fully inserted in the holding seats 51 and have an upright orientation so as to reposition the tubes 2 in the tube rack 3.

Specifically, in one embodiment, the device 1 can be configured in such a manner that each gripper 23 gripping a tube 2 can slide (slip) along the tube 2 when the mount 10 is moved in the first moving direction and the tube 2 can be fully inserted in a holding seat 51, i.e., can be placed on the seat bottom 64. Accordingly, tilted or non-tilted tubes 2 can simultaneously be gripped by the grippers 23 for repositioning the tilted tubes 2. This slipping engagement of the grippers 23 can, e.g., be obtained by choosing the elastic force of the leaf springs 45 of the gripping arms 40, 41.

As illustrated, in one embodiment, each of the grippers 23 can be configured to grip a tube 2 at least 20% of a length of the tube 2 below a top opening of the tube 2 in order to reliably process samples by avoiding contamination by the grippers 23.

As illustrated, the device 1 can further comprise a stopper 66 for stopping a tube rack 3 on a rack transport line 69 in a position in which the tubes 2 can be gripped by the grippers 23 to be repositioned in the tube rack 3. Here, the upright position of the tubes 2 can be aligned with the first and second moving directions of the mount 10 and grippers 23, respectively. Specifically, in one embodiment, the stopper 66 can comprise a stopper arm 70 pivotably fixed to the base 4 by stopper pivot joint 71 and resiliently coupled to the base 4 in a manner that the stopper arm 70 can be pivoted against a resilient force of stopper resilient means 67 such as, but not limited to, a helical spring. Specifically, as illustrated, in one embodiment, the stopper arm 70 can comprise a first stopper arm end 72 having a roller 54 attached thereto and a second stopper arm end 73 which can be moved to block or release a path of a tube rack 3 on the rack transport line 69. In one embodiment, the roller 54 can roll on a rolling face 61 projecting from the disk 36 in such a manner that the first stopper arm end 72 can be pivoted towards and away from the disk 36, with the movement of the first stopper arm end 72 away from the disk 36 being against the resilient force of the stopper resilienter 67. As a result, by rotating the disk 36, the second stopper arm end 73 can be pivoted into and away from a blocking position in which the transport of a tube rack 3 on the rack transport line 69 can be blocked. Accordingly, the transport of a tube rack 3 can readily be blocked and released according to the repositioning operation of the device 1.

Thus, with one single actuator 34, it can be possible to actuate a plurality of grippers 23, i.e. to move the grippers 23 in the first direction towards the holding seats 51 and in the second direction away from the holding seats 51, to rotate the gripper arms 41, 42 such as to move the gripper portions 42 towards each other to grip a tube 2 and away from each other to release a tube 2, and it can also be possible to actuate the stopper 66 for stopping a rack 3.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A device for repositioning tubes in a tube rack, the device comprising:
   a stationary base;
   a mount movable relative to the base in a first moving direction towards a tube rack and a second moving direction opposite to the first direction;
   at least one actuator for moving the mount;
   one or more grippers coupled to the mount and movable with the mount, each gripper comprising a pair of gripping arms provided with gripping portions for gripping a tube, wherein each gripper gripping a tube can slide along the tube in case the tube is fully inserted in a holding seat of the tube rack;
   at least one biasing element resiliently coupled to the mount and to the gripping arms in a manner to be movable relative to the mount and thereby move the gripping portions towards or away from each other; and
   at least one blocking element resiliently coupled to the stationary base configured to engage with the biasing element and to block movement of the biasing element with respect to the mount against a resilient force during a first period in which the mount is moved along a travel path in the first moving direction so as to move the gripping portions towards each other and configured to disengage from the biasing element while moving in the first direction after the mount has been moved along the travel path and before a second period in which the mount is moved in the second moving direction so as to allow the gripping portions to be resiliently moved away from each other, wherein the blocking element is a lever pivotably fixed to the base and configured such that the biasing element is or gets in contact with the lever during the first period and subsequently slides off the lever before the second period.

2. The device according to claim 1, wherein each gripping arm is resiliently deformable.

3. The device according to claim 2, wherein each gripping arms comprises a leaf spring arranged so that the gripping portion is resiliently bent relative to a fixing portion coupled to the biasing element.

4. The device according to claim 3, wherein the gripping portion is articulated to the fixing portion.

5. The device according to claim 1, wherein the mount comprises a first holding rod and a second holding rod and each gripper comprises a first gripping arm pivotably coupled to the first holding rod and a second gripping arm pivotably coupled to the second holding rod.

6. The device according to claim 5, wherein the biasing element is a biasing rod coupled to the gripping arms, wherein each gripping arm is coupled to the biasing rod in such a manner that movement of the biasing rod causes pivoting of the gripping arms around the first holding rod and second holding rod respectively.

7. The device according to claim 1, wherein the gripping portion of each of the gripping arms comprises a rubber pad for gripping a tube.

8. The device according to claim 1, wherein the actuator is an electric motor having an actively rotated rotor, wherein the rotor is coupled to an eccentric projection engaged with a guidance of the mount for moving the mount in the first and second moving directions.

9. The device according to claim 1, further comprising, a stopper configured to stop a rack transported on a rack transport line.

10. The device according to claim 9, wherein the stopper is a pivoted arm resiliently coupled to the base in a manner that the arm can be pivoted against a resilient force.

11. The device according to claim 1, wherein each gripper arms is configured in a manner to grip a tube at least 20% of a length of the tube below a top opening of the tube.

12. A system for repositioning tubes in a tube rack, the system comprising:
a tube rack holding one or more tubes; and
a device for repositioning tubes in a tube rack according to claim 1.

13. A process for repositioning a tube in a holding seat of a tube rack using a gripper, the gripper comprising a pair of gripping arms provided with gripping portions for gripping a tube, the process comprising:
moving the gripper in a first moving direction during a first period towards the holding seat, wherein at least one blocking element resiliently coupled to a stationary base of a device for repositioning tubes in a tube rack engages with a biasing element coupled to the gripping arms of the gripper and blocks movement of the biasing element with respect to a mount of the device for repositioning tubes in a tube rack against a resilient force during the first period in which the mount is moved along a travel path in the first moving direction so as to move the gripping portions towards each other to grip the tube, wherein the blocking element is a lever pivotably fixed to the base and configured such that the biasing element is or gets in contact with the lever during the first period and subsequently slides off the lever before the second period;
moving the mount in the first moving direction to disengage the biasing element after the mount has been moved along the travel path in the first moving direction so as to allow the gripping portions to be resiliently moved away from each other to release the tube;
moving the gripper in a second moving direction opposite the first moving direction, during a second period, after the first period.

* * * * *